United States Patent [19]

Bartos et al.

[11] 4,162,003

[45] Jul. 24, 1979

[54] READY-FOR-USE RAPID TEST PACKAGE FOR SEROLOGICAL TESTS

[75] Inventors: Dezsö I. Bartos, Buchenweg, 5024 Pulheim, Fed. Rep. of Germany; Jerzy Rybczynski, Kolding, Denmark

[73] Assignee: Dezsö István Bartos, Pulheim, Fed. Rep. of Germany

[21] Appl. No.: 888,041

[22] Filed: Mar. 16, 1978

Related U.S. Application Data

[63] Continuation of Ser. No. 793,653, May 4, 1977, abandoned, which is a continuation of Ser. No. 693,801, Jun. 7, 1976, abandoned, which is a continuation of Ser. No. 483,659, Jun. 27, 1974, abandoned.

[30] Foreign Application Priority Data

Jun. 30, 1973 [DE] Fed. Rep. of Germany ....... 2333434

[51] Int. Cl.² .................. B65D 25/08; F26B 5/04; F26B 5/06; G01N 31/00
[52] U.S. Cl. .................. 206/219; 23/230 B; 34/5; 34/15; 206/569; 424/8; 424/11; 424/12; 424/13
[58] Field of Search .................. 424/3, 8, 11, 12, 13; 23/230 B; 206/569, 219; 34/5, 15; 62/60

[56] References Cited

U.S. PATENT DOCUMENTS

| | | | |
|---|---|---|---|
| 3,415,361 | 12/1968 | Chambliss | 424/12 |
| 3,616,543 | 11/1971 | Barclay | 206/219 X |
| 3,825,410 | 7/1974 | Bagshawe | 424/12 X |
| 3,839,153 | 10/1974 | Schuurs | 424/12 X |
| 3,843,777 | 10/1974 | Hainski | 424/13 |

FOREIGN PATENT DOCUMENTS

| | | | |
|---|---|---|---|
| 2195 | of 1912 | United Kingdom | 424/13 |
| 1210819 | 11/1970 | United Kingdom | 424/11 |

OTHER PUBLICATIONS

BBL, Manual of Products & Lab. Procedures, BBL-of 8-D Cockeysville, Md., 5th. Ed. 1968, 3rd. reprint, 1970, pp. 66, 186.

Primary Examiner—Anna P. Fagelsoan
Attorney, Agent, or Firm—Sprung, Felfe, Horn, Lynch & Kramer

[57] ABSTRACT

A ready-for-use rapid test package for carrying out serological investigations in which at least two of the following reactants:

(1) patients serum;
(2) erythrocytes;
(3) amboceptors specific for the erythrocytes;
(4) complement and
(5) a reactant selected from the group consisting of antigen and antibodies not belonging to reactant class (3)

are reacted with each other, the package containing at least two of the reactants in a solid and preserved form, in quantities suitably adjusted to each other, to carry out the test.

The package provides the clinician or serological laboratory with reliable and simple means of carrying out the complement binding reaction without the complicated adjustments of the activities of the different reactants.

4 Claims, 10 Drawing Figures

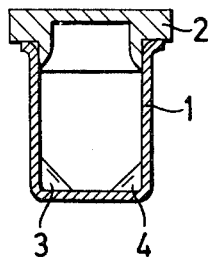
FIG. 1
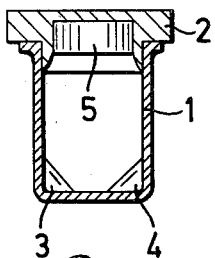
FIG. 2
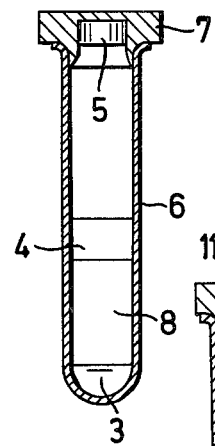
FIG. 3 FIG. 6
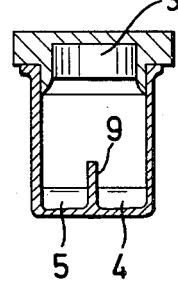
FIG. 4
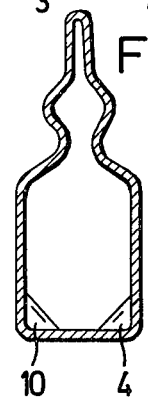
FIG. 5
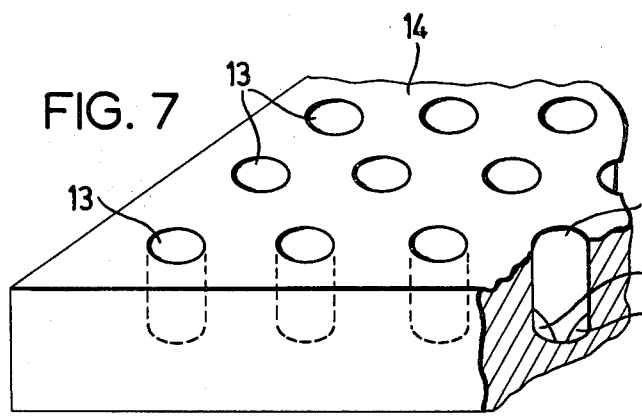
FIG. 7
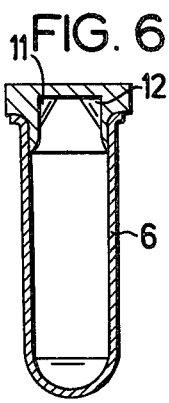
FIG. 10
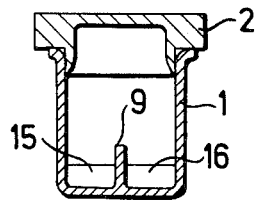
FIG. 8
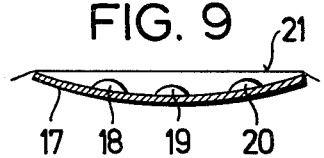
FIG. 9
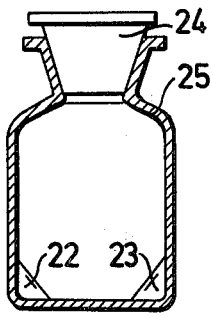

READY-FOR-USE RAPID TEST PACKAGE FOR SEROLOGICAL TESTS

This is a continuation of application Ser. No. 793,653, filed May 4, 1977, now abandoned, which in turn is a continuation of Ser. No. 693,801 filed June 7, 1976, now abandoned, which in turn is a continuation of Ser. No. 483,659 filed June 27, 1974, now abandoned.

SUMMARY OF THE INVENTION

This invention relates to a ready to use rapid test package for carrying out serological investigations, in particular for carrying out the complement binding reaction.

When foreign substances are taken in parenterally, the body frequently produces a defence reaction in which so-called antibodies are formed. Substances which provoke the formation of antibodies are known as antigens. These are usually mixtures of proteins or their degradation products, lipoids and polysaccharides, for example bacteria, viruses, blood corpuscles and toxins. The antibodies formed, which are also termed immune bodies in cases where the antigens have a cell damaging action, bind the antigens by a highly specific reaction. The presence of antibodies therefore results in a specific resistance of the organism to the corresponding antigen.

Because of their high grade specificity, antibodies can be used to identify the corresponding antigens. If the presence of certain immune bodies can be demonstrated in an organism, it can be concluded with a high degree of certainty that the organism has been exposed to the corresponding antigen. The method of detecting the antibodies is, in principle, extremely simple and comprises bringing a body fluid, for example blood, into contact with antigen. If an antigen-antibody reaction takes place, then this is evidence for the presence of the antibody. It is particularly important that evidence for exposure to antigens can be obtained via the corresponding antibodies in cases where the antigens are no longer present in the organism.

The detection of antibodies which belong to the group of lysins is frequently carried out by the so-called complement binding reaction. Lysins are antibodies which have specific bacteriolytic, virucidal, cytolytic or haemolytic properties which are demonstrated when they are brought into contact with the corresponding antigens in the presence of a non-specific component present in every normal serum, the so-called complement. Without the complement, the specific antibody remains inactive. Since lysins must combine with two substances to manifest their action, the antigen and the complement, they are known as amboceptors.

The complement or complement system (abbreviated K or C') is a labile serum function which, as far as is known today, comprises at least 10 serum enzyme factors and which loses its activity when heated to 56° C. for half an hour or when left to stand at room temperature. The possibility of inactivation of the complement system C' by heating is an essential part of the method of carrying out serological reactions. When a patient's serum which contains antibodies has been heated to 56° C. for 30 minutes, it can be mixed with the corresponding antigen without a reaction taking place. The reaction between antigen and antibody (in this case lysin, in other words an amboceptor) then occurs only when a system which contains complement is added, for example fresh, unheated serum.

The dependence of the reactions between antigens and amboceptors on the presence of complement can be demonstrated particularly impressively in the so-called haemolytic system. By haemolytic system is meant a system of erythrocytes and the amboceptors which are specific for these erythrocytes. In practice, the amboceptor used is a serum which contains only the amboceptor component and not any of the other reactants necessary for the antigen/antibody/complement reaction, in other words a serum which has been heated to 56° C. for sufficiently long to inactivate the complement system C'. The erythrocytes used are generally sheeps' erythrocytes and the specific amboceptor a complement-inactivated serum from a rabbit which has been sensitised to sheeps' erythrocytes. An erythrocyte suspension is first added to an amboceptor solution to obtain a suspension of erythrocytes in serum. When this is added to a serum which contains complement, generally a fresh guinea pig serum free from blood corpuscles, haemolysis takes place, i.e. the membranes of the sheeps' erythrocytes are destroyed after the addition of complement and the blood pigment goes into solution.

The reaction between the haemolytic system and the complement (by complement is always meant in the following text a fresh serum which contains complement) is therefore a true colour reaction which indicates the presence of complement both quantitatively and qualitatively. It is only in the presence of complement (disregarding the cases of spontaneous haemolysis which may occasionally occur and which will be discussed hereinafter) that the originally colourless to pale yellow solution containing the erythrocytes takes up blood pigment. The intensity of the red colour depends, within certain limits, on the quantity of activity of the complement. If the complement is present in large quantities or is highly active, haemolysis or deep colouring of the solution above the blood corpuscles takes place within a short time whereas, if only a small quantity of complement is present or if it is less active, the same haemolytic system will undergo only a small amount of haemolysis in the same time.

The haemolytic system is therefore a suitable indicator for reactions which require complement, i.e. it can serve as an indicator system for detecting the reactions of other antigens with their corresponding antibodies, in particular those antigen/amboceptor/complement reactions which are not so obvious in their appearance as haemolysis. The principle is very simple. The serum which is to be tested for the presence of antibodies and in which the complement has been inactivated (usually referred to as test serum or patient's serum) is brought together with the corresponding antigen, and the complement is then added. If the test serum does not contain specific antibodies for the antigen used, then the complement added is not used up. The complement is therefore still available for other antigen/complement reactions. If, therefore, the test system or test serum and antigen also contains the haemolytic system (which is added to the other component after incubation), then haemolysis takes place and the solution becomes coloured. The occurrence of haemolysis is taken as a negative test result, i.e. as a sign that no specific antibodies for the given antigen are present. If, however, the test serum contains antibodies which react with the given antigen in the presence of complement, then little or no complement is available for haemolysis. Haemolysis is therefore absent or attenuated. The absence of haemolysis in a system composed of test serum, antigen, haemolytic system and complement is therefore taken as a positive test result, in other words an indication that the test serum contains the antibodies corresponding to the given antigen.

The test method described above has become established in serological laboratories as the 'complement binding reaction' and is widely used to detect pathogens by way of their corresponding antibodies.

The complement binding reaction has become particularly important for the diagnosis of syphilis but it is also used to an almost similar extent to diagnose brucellosis, echinococcus, gonorrhoea, whooping-cough, leptospirosis, foot and mouth disease, mumps, pemphigus, rhinoscleroma, glanders, tuberculosis, toxoplasmosis, trichinosis and virus and other diseases.

Although the principle of the complement binding reaction described above is very simple, it is in practice very complicated to carry out as can be seen from the example of the syphilis test described below. This test generally requires five reactants or solutions of reactants which must be stored separately:

(1) The patient's serum (P) is obtained by running blood (generally venous blood) into a test tube, detaching the blood clot from the wall of the tube with a glass rod or a long platinum needle, and leaving the glass tube to stand overnight at a temperature of about 2° to 5° C. The serum usually separates as a clear fluid which can easily be pipetted off. Freshly drawn blood must not be immediately vigorously cooled and centrifuged because the serum is then liable to manifest non-specific inhibition of haemolysis. The serum which has been pipetted off is heated to about 56° C. for half an hour to inactivate the complement. It is generally diluted with five times its volume of 0.9% sodium chloride solution which should as far as possible be sterile.

(2) Sheeps' blood erythrocytes (E) are generally used as a 2 to 4% suspension of washed erythrocytes in physiological saline solution. Instead of the physiological saline solution, which is also used for washing, similar solutions may be used such as Kolmer or Osler-Strauss-Meier solution. The concentration of the suspension may be adjusted by various methods, in particular by the method of haematocrit determination.

(3) The haemolytic amboceptor (A) used to complete the haemolytic system (EA) is serum from a rabbit which has previously been exposed to sheeps corpuscles. The serum is complement-inactivated as described under (1). The haemolytic titre of the amboceptor should be at least 1:1000. By haemolytic titre is meant that dilution of guinea pig serum at which a given quantity of sheeps' blood corpuscles will be just completely haemolysed under certain standard conditions in the presence of a sufficient or excess quantity of complement. The titre is generally determined on a system of 0.5 ml of amboceptor dilution (serial dilution), 0.5 ml of complement dilution, 0.5 ml of 2% sheeps' erythrocyte suspension and 1.5 ml of diluent (physiological saline solution, Kolmer salt solution, Eagle solution or Veronal buffer solution) incubated at 37° C. for 60 minutes. The amboceptor should preferably have a titre of at least 1:4000, in other words it should still bring about complete haemolysis under standard conditions when diluted to 1:4000. The quantity of amboceptor used for the test is four times the quantity of amboceptor which causes solution after 1 hour.

(4) The complement (K) is fresh guinea pig serum. It is diluted immediately before use, e.g. with physiological saline solution. The quantity of complement required is determined by a method of serial dilutions similar to that indicated under (3), in which varying quantities of complement are added to a test system of test tubes containing suitably adjusted quantities of sheeps' erythrocytes (E) and haemolytic amboceptor (A), and the contents of each test tube are diluted to the same total volume (generally 3 ml) with diluent and incubated at 37° C. for 60 minutes. This method determines what is the least quantity of complement required to bring about complete haemolysis. The quantity used in practice is generally about twice this quantity.

(5) The antigen (AG) used for the complement binding reaction for syphilis is generally cardiolipin antigen or Reiters antigen. Cardiolipin is a phospholipid obtained from ox heart, which forms an antigen-antibody complex with the antibodies produced in response to the syphilis pathogen. The possibility of using cardiolipin is based on the fact that the antibodies produced in response to a given antigen will undergo an antibody-antigen reaction not only with the original virulent antigen but also with certain other antigens which are structurally extremely similar, for example antigens whose virulent action has been attenuated by certain chemical reactions. The specificity of the antibody is to that extent not absolute. This is of great importance in practice since it makes it possible for the presence of antibodies against highly dangerous or difficultly obtainable antigens to be tested by using substitute antigens.

The cardiolipin antigen ready for use may comprise e.g. a 0.0175% alcoholic solution of cardiolipin containing 0.0875% of lecithin and 0.3% of cholesterol, and is available commercially. It is generally used in a dilution of from about 1:100 to about 1:200. Other preparations of the cardiolipin antigen are also possible.

Reiter's antigen comprises preserved spirochaetes grown on culture medium and activated by ultra high-frequency sound. It is also available commercially and used in dilutions of between 1:2 and 1:8.

(6) Lastly, a stock of diluent must be kept in the serological laboratory. As already mentioned above, physiological saline solution may be used (0.9% or if sheeps' erythrocytes with high resistance to haemolysis are used then 0.85%). Instead of physiological saline solution, one may also use Kolmer solution which contains magnesium sulphate in addition to sodium chloride, or Eagles buffer solution, which contains a K/Na phosphate buffer in addition to sodium chloride, or an Osler-Strauss-Meier solution or similar solution. It is generally advantageous to use solutions which contain magnesium and/or calcium ions because the enzyme reactions of the complement binding reaction require divalent cations as co-factors. The diluted solutions generally contain additions of phenol (e.g. 0.3% by weight) to stabilise them.

The serological tests using the complement binding reaction are extremely difficult to carry out in practice, firstly because the reactants vary considerably in their activity from one batch to another and lose their activity with varying rapidity in storage and secondly because the activities of the reactants must be adjusted to each other. It is obvious that such adjustment of activities is necessary. If, for example, the test system contained considerably more complement than is required for releasing the reaction between the patient's antibodies and the antigen, then rapid haemolysis would take place in every case. The test would therefore be less sensitive or even meaningless. Conversely, in the presence of insufficient complement the test becomes excessively sensitive so that false positive results may be obtained. The same applies to the adjustment of concentrations of the two components of the haemolytic system as to the adjustment of concentrations of complement to haemolytic system. The erythrocyte suspension must also be adjusted to the amboceptor dilution. The amboceptor solution used for the test is usually adjusted so that it has about twice the minimum concentration which is required for complete haemolysis when an excess of complement is present. In the description given below it should always be assumed, unless expressly stated otherwise, that the reactants are brought together in adjusted quantities as described above. Mixtures of the reactants are expressed for the sake of simplicity in terms of the abbreviations of their components indicated above, for example "EAK" represents a mixture of sheeps' erythrocytes (E), amboceptor solution (A), sensitised against sheeps' erythrocytes, and complement (K) in suitably adjusted concentrations. The solutions E, A, K, P and Ag usually amount to about 0.25 ml.

To carry out the main test, i.e. the investigation of the patient's serum, the sytem PKAg is prepared in a test tube and incubated at 37° C. for 30 minutes. This first step of the main test is generally referred to as "binding". The haemolytic system EA is then added and the resulting PEAKAg system again incubated at 37° C. The time of the second incubation is generally also about 30 minutes but varies according to the exact concentration ratios. In cases of doubt, the incubation time required for the second step of the main test can be determined by a comparison experiment carried out on the serum of a healthy subject which is not auto-inhibiting. The haemolytic system (EA) is sensitised by incubation at 37° C. before it is added to the PKAg system.

Another test carried out in the same way as the main test but without antigen is used as so-called serum control. The serum control carried out on the PEAK system tests the patient's serum for any tendency to auto-inhibition since it is only when a serum with auto-inhibition is used that haemolysis fails or is attenuated even when no antigen is present. Additional preliminary incubation tests should be carried out to determine whether the systems (E) and (EA) show signs of spontaneous haemolysis, which would make them unusable for the complement binding reaction. A so-called system control should also be carried out to ensure that the EAK system undergoes haemolysis.

Determination of the degree of haemolysis is carried out visually or photometrically in known manner.

The necessity to prepare the experimental system from a plurality of solutions (6 solutions for the main test, 5 solutions for the serum control test) makes the complement binding reaction even more complicated to carry out than it would in any case be, because of the need to adjust the concentrations and activities of the various reactants to each other. It is well known that a large number of individual pipetting operations carried out in a test leads to experimental errors.

A simplification of the methods for carrying out the complement binding reaction has not previously been possible because the maintests and control tests (PEAKAg, PEAK, EAK, EA, E) in any case necessitate separate delivery of the reactants. There are, however, also other reasons why it was not possible to supply several of the reactants in one combined solution. Since the reactants differ considerably from each other in their stability, correct adjustment of the activities of the different reactants in a combined solution is maintained for only a limited period. Moreover, the reactants react with each other when present in one solution.

The problem therefore arose of providing the clinician or serological laboratory with reliable and simple means of carrying out the complement binding reaction without the complicated adjustments of the activities of the different reactants.

This invention relates to a ready-for-use rapid test package for carrying out serological investigations in which at least two of the following reactants:

1. patient's serum,
2. erythrocytes,
3. amboceptors specific for the erythrocytes,
4. complement and
5. antigen, or antibodies not belonging to (3), are reacted with each other. The rapid test package according to the invention contains at least two of the reactants 3 to 5 in a solid and preserved form and in quantities suitably adjusted to each other for carrying out the test.

It has now been found that large quantities of haemolytic amboceptor, complement and antigen (optionally antibody) adjusted to each other in their concentrations or activities can be stored in portions in rapid test packages preserved by deep-freezing or freeze drying without the reactants in the various rapid test packages undergoing any significant relative changes in activity in storage. It was also found that the loss of activity of the preserved reactants in a rapid test package is slight.

The development of a new process for carrying out the complement binding reaction is particularly important in this connection in this process at least two of the reactants 3 to 5 are preserved in a solid form and used together in suitably adjusted quantities. The process is preferably carried out as follows: A mixture containing all the reactants required for the reaction in suitably adjusted quantities with the exception of the erythrocytes is incubated for the purpose of the main tests and comparison tests of the complement binding reaction. A quantity of erythrocytes adjusted in known manner to the quantity of the other reactants is then added to the mixture and the mixture is again incubated. The incubation time is in each case about 10 minutes to 2 hours, preferably 25 to 65 minutes.

The main difference between the old process and the new process in the main test is that in the new process it is not the PKAg system but the PAKAg system which is subjected to the first incubation ('binding'). The sensitisation of the EA system by incubation is therefore omitted. The main difference between the old process and the new process in the serum control test is that in the new process the PAK system is subjected to the first incubation but not the PK system. The process described above may, of course, also be carried out with conventionally stored or freshly prepared reactants.

The rapid test package according to the invention is particularly suitable for carrying out serological tests, in particular by the new process.

The rapid test package according to the invention for reactants from groups 3 to 5 generally comprises a container and a sealing cap, both of which may have various forms. The container and preferably also the sealing cap, however, should be chemically inert towards the reactant solutions used. For example, glass containers sealed with the usual plastics stoppers or closure caps used for pharmaceutical packages are suitable. The container may also have several internal cavities for storing the reactants separately.

According to a preferred embodiment of the new rapid test package, it is designed as a disposable package which is used only once and serves also as a reaction vessel for carrying out the test. In this case, the new rapid test package is preferably in the form of the test tubes commonly used for carrying out the complement binding reaction and is made of glass or some other transparent material, and it contains the reactants in the quantities suitable for carrying out an individual test.

The reactants in the new rapid test package are preserved in the solid form, in particular by freeze drying or deep freezing at temperatures below −21° C. Freeze-dried reactants are particularly suitable as are also deep frozen solutions of the reactants which are rapidly frozen at temperatures below −30° C., preferably below −55° C. After they have been frozen, the reactant solutions should be stored at temperatures below −21° C., preferably below −40° C. and in particular below −55° C.

If the reactants in the new rapid test package have been preserved by deep freezing, they can be melted before use, e.g. by leaving them at room temperature, and then used in the same way as solutions prepared in the ordinary way, by adding the still missing solutions to them. If the reactants in the new rapid test package have been preserved by freeze-drying, they are brought into solution by the addition of solvents, for example physiological saline solution, or by the addition of other reactants in an excess quantity of solvent.

When individual reactants are freeze-dried, it may be advisable to add an inert carrier, for example human albumen. When individual reactants have been freeze dried, it is not necessary to use a solution with as large a quantity of solvent as would be required with the complement binding reaction is carried out in the conventional manner. In many cases, more concentrated solutions of the reactants can be used, thereby achieving more rational drying. In that case, the freeze-dried reactants, i.e. the residue obtained when a concentrated solution of reactants is freeze-dried, has a lower content of accompanying substances such as inorganic salts, for example, than would be required to prepare a ready-for-use solution of reactants by the addition of distilled water. When solvents are added to freeze-dried reactants it is therefore necessary to take into account the amount of accompanying substances present with these reactants, in particular the amount of inorganic salts. If all the reactants in the new rapid test package have been preserved in the freeze-dried form. it may be advisable, when delivering the rapid test package, also to include a diluent which has been adjusted in its concentration to the proportion of accompanying substances present with the reactants.

The reactants present in a rapid test package according to the invention are generally either all freeze-dried or all deep frozen but there is in principle no objection to using mixed forms of packages in which part of the reactants are deep-frozen and others freeze-dried.

In the case of freeze-drying it is generally desirable to introduce the salts required for the solution into the solvents supplied for carrying out the test because it has been observed that insufficient stability of freeze-dried reactants for the complement binding reaction is, to a large extent, due to the presence of salts and particularly to the presence of hygroscopic alkaline earth metal salts. If these salts are substantially eliminated from the freeze-dried reactants, the stability of the reactants is greatly increased.

In cases where the reactants are preserved by freeze-drying, it is advisable to adjust the individual solutions so that when they are melted and mixed, the resulting solution has a relatively low sodium chloride content, for example 0.85% by weight. In that case, increased resistance of the erythrocytes to haemolysis can to a certain extent be compensated without having to discard the erythrocyte suspension. When using erythrocytes with a normal sensitivity to haemolysis, it is generally desirable to have a total sodium chloride concentration of 0.90% by weight and, if the deep-frozen solution has a lower sodium chloride concentration, it can be adjusted to this value by adding sodium chloride concentrate.

The reactants are preferably kept separate from each other in the new rapid test package. This can be achieved, for example, by deep-freezing or freeze-drying the solutions of reactants in different areas of the rapid test package but it can also be achieved by first freezing one solution of reactant, covering it, for example with a physiological saline solution, freezing this separating layer and finally covering this frozen layer with another reactant solution. This should be carried out in such a way that the reactants do not mix to any significant extent. Separate storage of the various reactants can also be achieved by preserving part of the reactants in the sealing cap of the rapid test package (the term preserving will be used hereinafter to mean either freeze-drying or deep-freezing) and then preserving the remainder of reactants required in the test package, for example at the bottom of the package. There are other possible methods of keeping the reactants separate.

Separate storage of the individual reactants is important if the test package is required to remain suitable for use over a long period. If the rapid test package is to be used within a relatively short time, for example within a few days or up to one week after preparation separate storage is generally unnecessary. The length of time for which a rapid test package remains suitable for use when the reactants are all stored together should be determined in the individual case.

Although it is in most cases advantageous to store the individual reactants in the test package separately from each other because no reactions can then take place during storage, there is no objection to mixing freeze-dried reactants, especially if care has been taken to ensure that the residual moisture content of the freeze-dried substances is low. The residual moisture should generally be less than 1% by weight and preferably less than 0.5% by weight. When reactants are freeze-dried individually, it is also advantageous to store them at temperatures below room temperature, preferably below about 5° C. It is particularly advantageous to store even the freeze-dried products at temperatures below about −21° C., especially if they are intended to be stored for several years.

The concentrations or activities of the individual reactants in the new rapid test package are adjusted to each other in principle (qualitatively) in the same way as has been described above for the conventional process for carrying out the complement binding reaction. As regards the quantitative adjustment of the titre of the reactants, however, proportions different from those employed for the conventional process are particularly preferred. The amount of amboceptor used for the test is preferably at least about 25% higher than the usual amount. It is generally 5 to 16 times, and preferably about 6 to 10-times the quantity of amboceptor which will just cause solution if incubation is carried out for 60 minutes at 37° C. The complement may be used in quantities only about 10 to 25% higher than the complement unit. If desired, the process may also be carried out with the usual proportions of reactants (test quantities) employed for the conventional process, in particular with incubation times of about 30 to 100 minutes. The optimum incubation time can easily be determined.

The new test package may contain the combination of reactants AK, KAg, AAg and AKAg. As already mentioned above, it is in most cases advantageous to store the reactants separately. This applies especially to the storage of K and Ag which have a particular tendency to undergo non-specific reactions when stored together. The reactants in the combinations AK and AAg, on the other hand, can generally be stored quite satisfactorily together even when deep-frozen, provided they are not kept for more than about 9 months. If reactants are stored together, however, their keeping quality should be tested in the individual case.

Rapid test packages according to the invention which contain the combination of reactants AKAg (or AK antibody) are particularly important, i.e. combinations which contain all the reactants required for carrying out the complement binding reaction with the exception of the erythrocytes and the patient's serum. There are various possibilities of storing the combination AKAg, namely separate storage of all the reactants A/K/Ag, and partly separate storage in which one of the components is separated from the other two. For partial separation of the reactants in storage, the arrangements AK/Ag and AAg/K are suitable. The arrangement KAg/A is generally not possible owing to non-specific reactions between K and Ag. It may, of course, be carried out in individual cases if suitable preliminary tests in the case of a particular antigen have shown that K and Ag are compatible with each other in storage. The same applies to the combined storage of all three components, which is usually not possible. Moreover, as already mentioned above, reactants which are incompatible with each other can be stored together after they have been freeze-dried separately. Among the various arrangements for storage in the preferred embodiment of the invention which contains the combination of reactants AKAg, the arrangement AKAg and the arrangement A/K/Ag are particularly important.

In practice, the user of the rapid test package is generally provided with two variations of the rapid test package, namely one for carrying out the main test, which contains the reactants A, K and Ag, and another for carrying out comparison tests, which contains only two of the reactants. The reactants in the two types of rapid test packages are preferably taken from the same batch. Here again the embodiment of the invention in which components A and K are contained in a test tube is very advantageous. Preparation of the package is greatly simplified by the fact that only one type of test tube containing reactants is necessary. This test tube, which contains reactants A and K, is either sealed with a cap containing antigen to produce a test package for the main test or with an empty cap to produce a test package for the comparison test. The test package which contains all three reactants, the antigen being in the cap, may, of course, also be used for carrying out the comparison tests but this would entail unnecessary loss of antigen. When manufacturing the rapid test packages, it may be advisable to prepare caps with antigen for 40% of the test tubes which contain A and K.

If the serum of several patients is to be tested at the same time, several test packages for the main test and serum control may be set up pairwise in a test tube stand in which the various test systems are prepared and incubated. The test packages, may, of course, be supplied in stands for several parallel tests or the individual test systems for carrying out several parallel tests may be rigidly connected together, e.g. in the form of a spot plate. In that case, some of the spot recesses may contain the reactants A, K and Ag and others only A and K. Numerous variations of these arrangements are possible.

The description has so far been restricted to the use of new test package for detecting certain antigens by the presence of the corresponding antibodies in the patient's serum. The basic principle of detecting the formation of specific antigen-antibody complexes by the consumption of complement can, of course, be used for the reverse process, that is to say the antigen itself can be detected in the patient's serum if a specific antibody for this antigen is available. This method is particularly applicable to serum hepatitis (Australia antigen). The individual test package in this case contains test antibodies instead of the test antigen, for example an amboceptor specific for the Australia antigen in addition to the haemolytic amboceptor.

The rapid test package according to the invention may also be designed with several chambers under one sealing cap, one of which chambers, for example, may be used for carrying out the main test and another for carrying out the serum control. In that case the chambers may, for example, each contain an individual portion of the reactants required for carrying out the test, and the reactants of each individual portion should, of course, preferably be kept separate.

The test package according to the invention may contain an antigen combination instead of a single antigen. This provides a simple method of carrying out a so-called screening test on several pathogens.

For carrying out comparison tests, it may also be advantageous to use test packages according to the invention which, in addition to the components already mentioned above, contain, stored separately, preserved test positive patient's serum, weakly-positive patient's serum or test negative patient's serum.

The rapid test package according to the invention constitutes an exceptional advance in the field of applied serology. It makes an extraordinary large number of serological investigations available to a wide circle of users for the first time. When using the new rapid test package, tests based on the complement binding reaction are no more difficult to carry out than most of the present-day laboratory tests carried out in general medical practice. Screening, that is to say the precautionary routine testing of a large number of patients, therefore becomes possible on a scale which could hardly have been envisaged up to now because of the complexity of the measures required. In particular, the rapid test package according to the invention can improve the diagnostic facilities in areas which have no easy access to large diagnostic laboratories. But, even for the diagnostic laboratory itself the invention provides an important advance since the difficult and time consuming operations of measuring out the reactants and adjusting their activity can be carried out mechanically by the manufacturer so that the consumer, that is to say the serological laboratory, is relieved of the burden of this very time-consuming labour. It is particularly for laboratories which carry out serological work that the grouping of several test packages in one unit which enables several patients' serum to be tested side by side is of great importance.

Typical examples of embodiments of the rapid test packages according to the invention are illustrated in the accompanying drawings.

DESCRIPTION OF THE DRAWINGS

FIG. 1 is a cross-section through a rapid test package consisting of a glass container 1 of about 10 cc capacity sealed with a plastics cap 2. The rapid test package of FIG. 1 contains an amboceptor 3 which is specific for sheeps' erythrocytes and a guinea pig complement 4, both deep-frozen. Amboceptor 3 and complement 4 are kept separate from each other by holding the test package at a slant when introducing and deep-freezing the complement and then slanting it in the opposite direction when introducing and deep-freezing the amboceptor. The haemolytic amboceptor is rabbit serum from a rabbit sensitised to sheeps' blood corpuscles in a known manner and then complement-inactivated. The amboceptor (0.1 ml) was diluted by 1:250 and had a titre of 1:4000. The guinea pig complement (also 0.1 ml) was diluted by 1:9 and had a titre of 1:90.

Since the complement had a titre of 1:90 (determined on 0.5 ml samples, using 2% erythrocyte suspensions), 0.1 ml of complement diluted to 1:9 correspond to two complement units, that is to say twice the minimum quantity necessary for a complete solution. since an amboceptor with a titre of 1:4000 was used (the titre being based on 0.25 ml of solution, which together with 0.25 ml of erythrocyte suspension makes up the 0.5 ml of haemolytic system used for standardisation), 0.1 ml of amboceptor diluted to 1:250 correspond to about 6.4 amboceptor units, that is to say 6.4 times the dose of amboceptor which will just cause solution when incubated at 37° C. for one hour.

FIG. 2 shows a rapid test package which, like the package of FIG. 1 consists of a container 1 sealed with stopper 2 but which, in addition to amboceptor 3 and complement 4, contains antigen 5. The antigen 5 is kept separate from the outer reactants 3 and 4 in a deep-frozen form in a cavity in the sealing cap 2 which is open to the interior of the package. Amboceptor 3 and complement 4 are kept separate from each other in the same way as in FIG. 1. The quantities of amboceptor and complement and their ratios of concentration and activity correspond to those of FIG. 1. Antigen 5 (0.5 ml) was a commercial cardiolipin antigen 1:150.

Another example of the rapid test package according to the invention is similar in arrangement to that of FIG. 2 but, instead of 0.1 ml of amboceptor diluted as indicated above, 0.1 ml of the same amboceptor solution diluted by 1:6.5 with 0.55 ml of 0.85% physiological saline solution was used.

FIG. 3 shows a rapid test package according to the invention in the form of a reaction vessel for carrying out the test. It consists of a glass test tube 6 with cap 7 basically the same as cap 2 with a similar cavity. The test tube contains 0.1 ml of complement (dilution and titre as indicated above) frozen into the bottom of the test tube at −35° C. The complement is covered with 0.55 ml of 0.85% physiological saline solution 8. The physiological saline solution in turn is covered with 0.1 ml of amboceptor (dilution and titre as indicated above). 0.5 ml of antigen (Reiters antigen 1:8) are frozen in the cavity of cap 7. The rapid test package contains nitrogen as protective gas.

FIG. 4 shows a rapid test package similar to that of FIG. 2 but with the reactants at the bottom of the package separated by a partition 9. Reference numerals 3 to 5 have the same meaning as in FIGS. 1 to 3.

FIG. 5 shows a rapid test package according to the invention in the form of an ampoule. It contains a mixture 10 of 0.1 ml of amboceptor 1:50 and 0.1 ml of complement 1:9 with 0.8 ml of 0.85% physiological saline solution and a solution of 0.5 ml of cardiolipin antigen 1:150 and 0.8 ml of 0.85% physiological saline solution.

FIG. 6 shows a rapid test package according to the invention in which two reactants are stored separately from each other in the cavity of the sealing cap, namely a deep-frozen solution 11 of 0.1 ml of amboceptor 1:50 and 0.4 ml of 0.85% physiological saline solution and another deep-frozen solution of 0.1 ml of complement 1:9 and 0.4 ml of 0.85% physiological saline solution. The test tube 6 contains a solution of 0.5 ml of commercial Reiter antigen 1:8 ml of 0.85% saline solution.

FIG. 7 shows rapid test packages according to the invention combined in a spot plate. Each of the bores 13 in a polymethacrylate plate 14 constitutes a rapid test package according to the invention. Each bore contains separately stored reactants arranged as in FIG. 1.

FIG. 8 shows a rapid test package according to the invention which is similar to that of FIG. 4 but contains freeze-dried amboceptor 15 and freeze-dried complement 16. Freeze-drying was carried out by taking up 0.1 ml of complement (dilution and titre as above) with a solution of 0.0025 g of human albumen in 0.5 ml of water and introducing it into one of the chambers formed by partition 9 inside the package. The method was repeated with 0.1 ml of amboceptor solution (dilution and titre as above), using the other chamber. Freeze-drying itself was carried out in known manner at an initial temperature of about −50° C.

The rapid test packages according to the invention have been illustrated above with the quantities of reactants which are normally preferred for carrying out an individual test. In the complement binding reaction, however, the absolute quantities of the reactants are not important, provided that the quantities of the individual reactants are adjusted to each other. An individual test can therefore in principle be carried out with any multiple of all the reactants. Rapid test packages for micro tests (up to 0.1 ml total volume of all the reactants) are therefore in principle the same as those of FIGS. 1 to 8 but contain, for example, one twentieth of the quantities of reactants. A flat watch glass shaped dish as shown in FIG. 9, for example, is particularly suitable for carrying out tests on a micro scale. The dish 17 has a diameter of about 2 cm and contains amboceptor complement and antigen as deep-frozen drops 18 to 20 of their solutions in quantities suitably adjusted to each other for carrying out the complement binding reaction. The dish is covered with a piece of plastics adhesive tape 21. Spot plates are also very suitable for this purpose. Just as the quantities of reactants in the rapid test package can be reduced in scale, so also larger quantities may be used in a package.

FIG. 10 shows a rapid test package which contains 50 ml of amboceptor 22 (dilution 1:1250, titre 1:4000) and 50 ml of complement 23 (dilution 1:45, titre 1:90) in a glass reagent bottle 25 sealed with a plastics stopper 24.

All the packages of the examples with the exception of the package shown in FIG. 8 contain the reactants in a deep-frozen form.

The new process for carrying out the complement binding reaction and method of handling the rapid test package are explained by the following examples with reference to the rapid test package shown in FIG. 3.

To carry out the main test, a test package according to the invention is taken from the deep-freezer and thawed by immersing it in a water bath at 37° C. Thawing forms the solution AKAg to which 0.25 ml of patient's serum (method of obtaining see above) are added. The resulting solution of PAKAg is then incubated at 37° C. for half an hour. A binding reaction takes place if the patient's serum contains antibodies, in this case syphilis antibodies. The complement is used up with formation of antigen-antibody complex. This step of the process differs from the corresponding step in the conventional method of carrying out the complement binding reaction in that the haemolytic amboceptor is already present during the binding reaction.

After the half hour's incubation period, 0.25 ml of the 2% sheep's erythroycte suspension are added to the system and the system is again incubated at 37° C. The incubation time in this second step is also half an hour but depends on the exact adjustment of the reactants to each other and since this is carried out by the supplier of the individual package, directions should be supplied with the package as to the correct incubation time. The time is generally 30 minutes but can be determined by a comparison test with non-inhibiting serum from healthy subjects.

After the second incubation period, the result, i.e. the degree of haemolysis of the preparation, is assessed visually or photometrically in known manner.

Comparison tests are virtually essential for carrying out serological investigations. The comparison tests described above can be carried out very elegantly with the individual test package according to the invention. The control tests are also carried out by the new process as follows:

To carry out the serum control (auto-inhibition test) an individual test package is taken from the deep freezer and the sealing cap which contains the antigen is removed. The contents of the test tube are then melted in a water bath at 37° C. to form liquid solution AK. The same quantity of patient's serum as in the main test is added to this solution and the solution is madeup to the same volume as in the main test by the addition of physiological saline solution. To keep the reaction conditions as close as possible to those of the main test, the resulting system of PAK is then incubated at 37° C. for half an hour and then incubated for a second time after addition of the erythrocyte suspension in the same way as in the main test. The interpretation of the result is carried out in the same way as in the conventional serum control test.

System control in system EAK is carried out on the same principle as the serum control. The cap containing the antigen is removed but no patient's serum is added.

There remain the control tests in system EA and E. The erythrocyte suspension E can, of course, quite easily be tested for spontaneous haemolysis under incubating conditions but the individual test package according to the invention is not necessary for this. To test the system EA which must not show any signs of haemolysis under incubating conditions, the sealing cap which contains the antigen is removed and the contents of the test tube are melted in a water bath at 56° C. and kept at this temperature for 20 minutes. The remaining solution A is cooled to room temperature, erythrocyte suspension is added, and the system is then incubated at 37° C. for about 30 minutes. The test on system EA can generally be omitted because spontaneous haemolysis, that is to say haemolysis in the absence of complement, is extremely rare in this system. A test carried out on system EA to test the amboceptor for the presence of traces of complement is unnecessary because the amboceptor has, of course, been tested by the manufacturer.

We claim:

1. A disposable package comprising a chemically inert transparent reaction vessel for performing a serological complement fixation test which contains reactants for said test comprising an antigen or antibodies to the antigen to be detected, hemolytic amboceptor and complement, said reactants being preserved in said vessel in frozen or freeze-dried form, each having been deep frozen or freeze-dried to form a separate layer or having been deep frozen or freeze-dried in separate areas of said vessel.

2. The package of claim 1, wherein the reactants, hemolytic amboceptor and complement are frozen in layers on the bottom of the vessel and separated by a frozen layer of physiological saline.

3. The package of claim 2, having a sealing cap wherein the reactant antigen or antibodies are frozen in the cavity of the sealing cap.

4. The package of claim 1, wherein the reactants are freeze-dried after the addition of albumen.

* * * * *

UNITED STATES PATENT AND TRADEMARK OFFICE
CERTIFICATE OF CORRECTION

PATENT NO. : 4,162,003
DATED : July 24, 1979
INVENTOR(S) : Dezso Istvan Bartos, et al.

It is certified that error appears in the above–identified patent and that said Letters Patent are hereby corrected as shown below:

On Title page, under "OTHER PUBLICATIONS" after "BBL" second occurrence, delete "-of 8" and insert --Div of B--.

Column 12, line 26, "and 0.8" has been omitted after "1:8".

Signed and Sealed this

Eleventh Day of December 1979

[SEAL]

Attest:

*Attesting Officer*

SIDNEY A. DIAMOND
*Commissioner of Patents and Trademarks*